United States Patent [19]

Moore et al.

[11] Patent Number: 5,656,813

[45] Date of Patent: Aug. 12, 1997

[54] APPARATUS FOR IMAGING GAS

[75] Inventors: Gerald Moore, Boggs Township, Armstrong County, Pa.; James G. Hawley, San Jose, Calif.; William C. Bradley, Gastonia, N.C.; Brian M. Harper, Wildmoor, England

[73] Assignee: GMD Systems, Inc., Pittsburgh, Pa.

[21] Appl. No.: 417,074

[22] Filed: Apr. 4, 1995

[51] Int. Cl.$^6$ ............................................. G01N 21/35
[52] U.S. Cl. .................................... 250/330; 250/338.5
[58] Field of Search ................................. 250/330, 332, 250/333, 342, 339.14, 338.5

[56] References Cited

U.S. PATENT DOCUMENTS

| | | | |
|---|---|---|---|
| 3,563,658 | 2/1971 | Dreyfus | 356/97 |
| 3,662,171 | 5/1972 | Brengman et al. | 250/83 |
| 3,715,497 | 2/1973 | Cooper et al. | 178/6.8 |
| 4,227,210 | 10/1980 | Nixon | 358/113 |
| 4,390,785 | 6/1983 | Faulhaber et al. | 250/330 |
| 4,543,481 | 9/1985 | Zwick | 250/339 |
| 4,555,627 | 11/1985 | McRae, Jr. | 250/334 |
| 4,670,653 | 6/1987 | McConkle et al. | 250/330 |
| 4,693,615 | 9/1987 | Kyriakis | 374/129 |
| 4,725,733 | 2/1988 | Horman et al. | 250/339 |
| 4,937,447 | 6/1990 | Barrett | 250/339 |
| 4,963,742 | 10/1990 | Abernathy | 250/338 |
| 4,963,744 | 10/1990 | Matthys | 250/343 |
| 4,965,447 | 10/1990 | Bly et al. | 250/233 |
| 4,967,276 | 10/1990 | Murakami et al. | 358/183 |
| 5,306,913 | 4/1994 | Noack et al. | 250/330 |
| 5,430,293 | 7/1995 | Sato et al. | 250/330 |

OTHER PUBLICATIONS

Moore, Gerald, "Visual display of Toxic Gas Emissions Using a Gas Imaging Camera System", 9 pp., Fall 1991, (attached to cover sheet entitled New Product Development Memo) no month.

Pratt, W. "Digital Image Processing", John Wiley & Sons, (1978) p. 319.

*Primary Examiner*—David P. Porta
*Assistant Examiner*—Richard Hanig
*Attorney, Agent, or Firm*—Webb Ziesenheim Bruening Logsdon Orkin & Hanson, P.C.

[57] ABSTRACT

An apparatus which remotely visualizes and detects toxic, flammable and other gas leaks and enables one to see gas clouds in real-time. A dual band thermal imaging infrared video camera fitted with a special filter images gas clouds. Image processing is utilized to develop and colorize the gas cloud information for display. The gas image is superimposed over a background image provided by a co-located visible light video camera.

39 Claims, 4 Drawing Sheets

APPARATUS FOR IMAGING GAS

BACKGROUND OF THE INVENTION

1. Field of the Invention

This invention relates to infrared radiation detection and, more particularly, to infrared video cameras and associated processing systems for visualizing gas clouds on a video display.

2. Background Art

There are literally thousands of chemical processes and systems which need continuous monitoring to ensure the safety and health of both site workers and the general populace. It is common for chemicals, either during the manufacturing process or in the bulk distribution thereof, to be stored for long periods of time, moved about an area, transferred from container to container or transported in long pipelines. Unfortunately, it is not uncommon for chemicals to be stored or transported in deteriorating tanks or pipes. The chance of spills and accidental releases of chemicals to the environment seems to rise every day. There is a clear need not only for a range of monitoring techniques to deal with early detection and subsequent tracking of accidental spills or leaks, but also for routine monitoring of chemical plants and storage areas.

Current monitoring techniques become inadequate when gases are involved because of the ability of most gases to travel unseen far past the point of original detection. The wind alone can make the path of release a matter of guess work and even the point of origin a matter of doubt. What is needed is a method in which escaping gases can be made visible to the eye and use the superior ability of human vision to gauge location and general movement. Once visible to the human eye, the gas image can then be subjected to processes of automation, such as machine vision, to aid in the monitoring and detection process.

Considerable effort has been expended in the past in the application of thermal imaging to gas detection. Optical techniques in general, based upon the absorption or emission of infrared radiation by gases and vapor, have been continuously developed for many years. Today, it is possible to use laser and non-laser systems to make precise concentration measurements along beam paths. However, there are few practical systems for obtaining an image of a gas cloud and, hence, for obtaining a real-time representation of the dynamics of the gas cloud.

One present technique for measuring gas is known as backscatter absorbing gas imaging, and uses an infrared video camera, together with a laser, to raster scan and illuminate the scene. The laser beam passes out through the camera optics in the reverse direction to the incoming radiation and the backscatter radiation from the background (terrain, buildings, etc.) behind the gas cloud is detected by the camera. The gas is detected by its absorption relative to the background. These systems offer good sensitivity and signal-to-noise ratios. However, they use a cooled infrared video camera which requires a separate source of cooling, such as a compressor, a bottle of liquified coolant or a thermoelectric cooler to operate. The cooled camera not only adds considerably to the expense of the system, but also increases maintenance and reduces the portability of the system. In addition, there are limitations imposed on the use of lasers, an active element in the system, which severely limits the overall utility of these systems. Only gases which have absorption features coincident with the laser ($CO_2$, He—Ne, etc.) can be detected. The essential laser also adds to the cost and complexity of the system. Presently, the range of these systems is not very large and, perhaps the biggest disadvantage of all is that the systems cannot image against a sky background. U.S. Pat. No. 4,555,627 shows one arrangement of a backscatter absorbing gas imaging system.

Other systems for detecting gases, chemicals or the like are shown, for example, in U.S. Pat. Nos. 3,563,658; 3,662,171; 3,715,497; 4,227,210, 4,390,785; 4,543,481; 4,670,653; 4,725,733; 4,937,477; 4,963,742; 4,963,744; 4,965,447 and 4,967,276.

It is not uncommon to process the output signals generated by infrared video cameras to enhance the desired signal and remove unwanted noise. The prior art processing has been generally limited to integration and subtraction techniques which limit the high noise levels inherent in infrared video cameras. Integration has classically been used to reduce the quantity of random noise present in the signal. However, the chief failing of integration is that it also prevents the quicker and more transient features of the desired signal from being seen. For example, the edges of gas clouds and the areas subjected to wind may be effectively integrated from the signal. Subtraction of consecutive frames from each other has also been used to separate the moving portions in the image from the stationary portions, using the assumption that the gas cloud moves while the background image does not. A major limitation of subtraction techniques is that often the gas cloud moves so slowly that it, in addition to the background, is removed. Subtraction alone can do nothing to reduce the noise when the noise resembles gas in its ability to change from frame to frame.

The primary difficulty of the prior art techniques is that they are not adequate to separate the signal from the noise in a gas imaging system. A vague image of the gas cloud might be visible after processing, but it is not sufficient to permit accurate and reliable detection, particularly by automatic methods. Accordingly, it is an object of the present invention to provide enhanced processing techniques on the output of an infrared video camera or the like to provide a better signal-to-noise ratio and a more accurate image of a moving gas cloud.

It is a further object of the present invention to provide a passive, non-laser based, preferably uncooled, infrared video camera detection system for accurately and inexpensively imaging a moving gas cloud.

SUMMARY OF THE INVENTION

Accordingly, we have developed an apparatus for generating a visible image of a gas cloud against a background scene. The apparatus preferably includes a visible light video camera and an infrared video camera, such as a pyroelectric infrared video camera, which view substantially the same scene. A chopping filter is associated with the infrared camera and alternately presents first and second band pass filters which pass radiation of two different infrared wavelengths to the infrared video camera. The first band pass filter passes infrared radiation at a measuring or strongly absorbing infrared wavelength for a predetermined gas. The second band pass filter passes infrared radiation at a reference or weakly absorbing infrared wavelength for the predetermined gas. The apparatus also includes an image processor responsive to an output from the infrared video camera for reducing noise and enhancing an information signal generated by a detected gas cloud. An overlay means combines an output from the visible light camera with an output from the image processor and produces a signal representing an image of the gas cloud superimposed upon the visible image of the background scene. Finally, the apparatus includes a display means, such as a monitor, for displaying the signal generated by the overlay means.

It is preferred that the reference wavelength of the second band pass filter be close to the measuring wavelength of the first band pass filter. The chopping filter can be a rotating disc having separate first and second band pass areas therein, such as a thin, circular wafer of a semiconductor substrate having layers of material deposited thereon to form the band pass filter areas. The band pass filter areas can be formed in the shape of nested, outwardly tapering archimedian spirals separated by about 180°. In a preferred embodiment, the chopping filter satisfies the equation:

$$N_B(\lambda_M)=N_B(\lambda_R),$$

where $N_B$ is the spectral radiance of the background scene, $\lambda_M$ is the measuring wavelength and $\lambda_R$ is the reference wavelength. This condition can be achieved by control of the density of the filter areas during manufacture.

A preferred image processor includes a storage means for storing at least one prior output frame of the infrared video camera. The image processor also includes a comparison means for comparing the current output frame of the infrared video camera with a prior frame in the storage means and generating a difference signal representing differences between the current frame and the prior frame. The image processor also includes a convolution means responsive to the difference signal from the comparison means for determining, on a pixel by pixel basis for each frame, whether a particular pixel should be further activated based upon a spatial relationship of activated pixels in a surrounding matrix of pixels, including the particular pixel. Finally, the image processor includes a temporal means responsive to an output generated by the convolution means for activating a pixel only if that pixel is activated in the current frame and was activated in a predetermined number of consecutive prior frames.

The image processor can further include a threshold means responsive to the difference signal from the comparison means for supplying to the convolution means only difference signals which exceed a predetermined threshold level. The image processor can also include an integrator means responsive to the output of the infrared video camera for integrating at least two frames of the infrared video camera output before supplying the frame for storage in the storage means and before supplying the current frame to the comparison means. In addition, the image processor can include a sustainer responsive to an output from the temporal means for maintaining each activated pixel in a frame as activated for a predetermined period of time beyond the duration of the frame. The image processor can further include a control means for establishing: (1) the rate of frame integration for the integrator means; (2) the rate of storage of frames in the storage means; (3) the threshold level of the threshold means; (4) the spatial filtering method used in the convolution means; (5) the number of consecutive prior frames considered in the temporal means; and (6) the period of time of the sustainer.

In a preferred embodiment, the convolution means examines a spatial relationship of an n×n array of pixels, such as a 3×3 array of pixels, including the particular pixel under consideration. In this preferred embodiment, the particular pixel in a frame is activated only if the three pixels in a left-hand column of the pixel array are each activated. The image processor can further include, in a feedback loop from the infrared video camera output to the infrared video camera, a whole picture averager which monitors the baseline brightness level of the infrared video camera. In response to any drift in said baseline brightness level, the whole picture averager adjusts a black level control in the infrared video camera to maintain an overall brightness level therein at a substantially constant level. Preferably, the baseline brightness level is generated by summing the amplitude values of all pixels in one or more frames and dividing the sum by the number of frames utilized.

DESCRIPTION OF THE PREFERRED
EMBODIMENTS

The present invention preferably uses a pyroelectric infrared video camera for detecting the infrared radiation characteristic of the gas cloud under observation. The pyroelectric infrared video camera is a passive device, requires no coolant, is relatively inexpensive, requires little maintenance and can operate for extended periods of time in many different environments. A pyroelectric infrared video camera operates by changes in optical power absorbed by a pyroelectric crystal which is the sensing element on the faceplate. The pyroelectric infrared video camera can be provided as a vidicon version which includes a single, large pyroelectric element which is raster scanned or as a recently developed array version which includes a 256×256 array of separate pyroelectric elements. The array version may prove to be preferred. Variations with time in the temperature of the pyroelectric material give rise through the pyroelectric effect to variations of surface charge. By sampling the charge, changes in temperature of the material may be measured. To a first order of approximation, the charge signal is proportional to the rate of change of the temperature of the material. The output signal of a pyroelectric infrared video camera in the vidicon version is generated by scanning the target material in a television raster by an electronic beam readout and in the array version is generated in a CCD readout with each separate element generating a separate pixel signal.

All pyroelectric cameras have a common property which is different from most other cameras. A steady flux of incident radiation on the detector, i.e., the pyroelectric material, will cause the detector to reach thermal equilibrium. Under these conditions, redistribution of charge through displacement currents will take place until there is no resultant charge and, hence, zero output signal. In order to provide a constant output signal, the radiation flux must be modulated. It is common in some pyroelectric cameras to provide a rotating chopper which alternately passes the radiation to the camera and stops the radiation from traveling to the camera. Others need to scan the scene to provide modulation. In the arrangement disclosed herein, a specially designed rotating chopping filter is used. This chopping filter takes advantage of the unique property of the pyroelectric detector and will be described hereinafter in more detail.

In accordance with the present invention, the chopping filter, in conjunction with the pyroelectric infrared video camera and a special image processor, provides an image of the gas cloud. This image is combined with a normal, visible light video image to provide an actual, real-time picture of a gas cloud. The gas cloud can actually be seen drifting through a plant or other facility. This video image can be captured with a video cassette recorder to be reviewed and analyzed at a later date.

Figure 1:
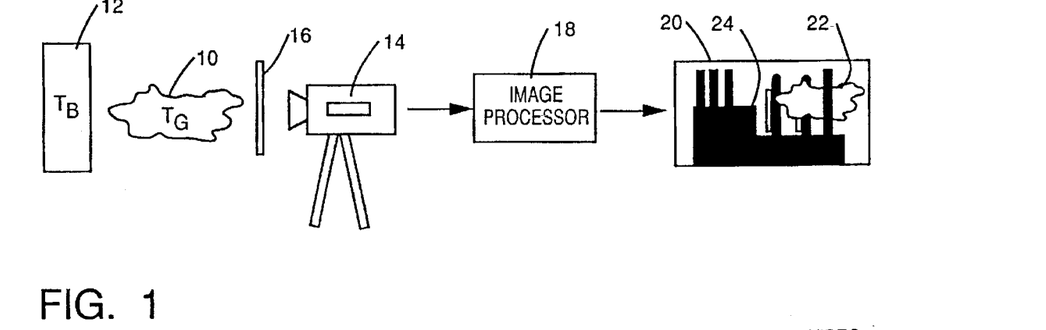
FIG. 1 is a schematic diagram showing the spectral imaging principles utilized in the present invention.

The principles by which a gas can be detected using a filtered infrared video camera in accordance with the present invention is shown in FIG. 1. A gas cloud 10 is viewed against a background object 12, which can be the sky, buildings and the like. As long as there is an effective temperature differential between the background temperature $T_B$ and the gas cloud temperature $T_G$, there will be either absorption or emission of radiation by the gas cloud and the gas cloud will have unique spectral properties. The gas cloud produces a spectral unbalance since it absorbs radiation at certain characteristic wavelengths but not at other wavelengths and replaces it with radiation related to the temperature of the gas. If a camera 14 is fitted with a filter 16 that matches a strongly absorbing wavelength of a particular gas, a sharp change in energy will be noted if that gas is present. Only in the extreme case where effective $T_B$=effective $T_G$ will no differential signal exist, preventing the gas from being imaged. In practice, particularly in industrial applications, significant temperature differentials nearly always exist.

In a complete system, the gas imaging infrared camera is combined with a visible light video camera, both preferably included in camera 14, and both video signals are supplied to an image processor 18. The radiation transmitted to the visible light video camera is not subjected to the special filtering represented by filter 16. As will be explained hereinafter in more detail, the output signal of the infrared video camera is processed to reduce noise and enhance the image detected thereby, and is then combined with the signal generated by the conventional, visible light video camera. The processor 18 supplies its output signal to a monitor 20 or the like, which displays the gas cloud as a brightly colored overlay 22 superimposed on a black and white image 24 from the visible light video camera. This final presentation of elements identifies the position, size, direction and magnitude of the leak or gas cloud directly against the background from which it emanates. This exact positional identification allows the source of the leak to be pinpointed as well as show the extent of the diffusion of the gas cloud.

Figure 2:
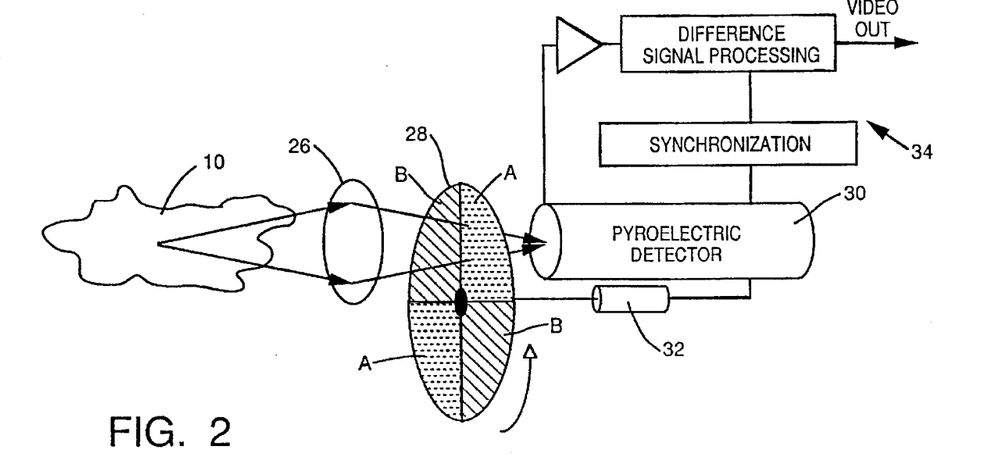
FIG. 2 is a schematic diagram showing the principles of using a chopping filter in accordance with the present invention with a pyroelectric vidicon camera.

The principles of operation of the present system are shown in more detail in FIG. 2. The infrared energy radiated by the gas cloud 10 passes through a lens 26 and through a rotating chopping filter 28 to a pyroelectric detector 30 (vidicon tube or detector array) in the pyroelectric camera. The filter 28 is rotated in a controlled manner by a motor 32 contained within the housing for the pyroelectric camera. An advantage of this arrangement is that an on-off chopper filter provided in standard pyroelectric infrared video cameras can be readily removed and replaced by the chopping filter 28 of the present invention. The signals developed by the pyroelectric detector 30 are subjected to standard synchronization, amplification and difference signal processing, generally referred to by reference number 34, to generate the output video signal from the pyroelectric camera.

As a general proposition, the chopping filter 28 provides the same function as the prior art chopper, but adds wavelength specificity or spectral filtering. The chopping filter 28 includes two distinct filter areas which provide alternate scans at a measuring wavelength and at a reference wavelength. All other considerations of chopping are still present, though, including the need for flicker processing which comes from the alternating field inversions. The chopping filter 28 is constructed specifically for detecting a particular gas. The measuring wavelength is selected as a strongly absorbing infrared wavelength for the gas in question. The reference wavelength is selected as a weakly absorbing infrared wavelength for the gas in question, preferably at a wavelength close to the measuring wavelength. The filter 28 is then constructed with alternating band pass filter areas tuned to the measuring and reference wavelengths. Transmissions of radiation at the two different wavelengths produce the differential signal needed for the operation of the pyroelectric camera. The preferred closeness of the measuring and reference wavelengths will minimize imaging from objects having large temperature differentials from the environment, but not related to the gas in question. The two different filter areas on the chopping filter 28 are represented in FIG. 2 as areas A and B.

Figure 3:
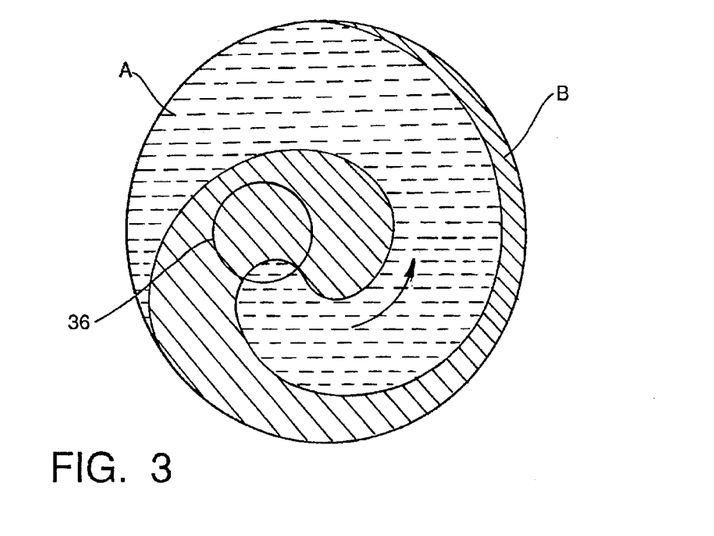
FIG. 3 is a plan view of a preferred chopping filter in accordance with the present invention.

A preferred construction of the chopping filter is shown in FIG. 3. The filter is a thin, circular wafer or substrate of silicon or other semiconductor material and includes two separate filter sections in a type of yin-yang shape, also referred to as a pair of nested, outwardly tapering archimedian spirals separated by about 180°. The filters are constructed by known vapor deposition techniques in which multiple layers of certain materials at particular thicknesses are deposited on the substrate to form band pass filters at the desired wavelengths. One filter area is designed to pass radiation at the measuring wavelength and the other filter area is designed to pass radiation at the reference wavelength. The twin spiral shape is advantageous in facilitating a desired top to bottom wiping action across the thermal imaging material of the pyroelectric infrared camera. (The position of the detector with respect to the filter is shown in FIG. 3 as a circle identified by reference number 36.) This wiping action duplicates that of a standard chopper for the same reason of inducing change information into the tube. This shape of the chopping filter 28 is also preferred since the electron scanning beam in the pyroelectric vidicon camera version must first track one wavelength and then the other. The rotational frequency of the chopping filter 28 is determined by the scanning rate of the pyroelectric camera. For each field scan, the electron beam must read off signals which are due to one wavelength. The shape of the filter 28 ensures that these conditions are satisfied.

When the pyroelectric camera is fitted with the chopping filter 28 discussed above, the camera functions as a spectrophotometer in that it responds only to changes at particular wavelengths. This wavelength sensitivity is the heart of the ability of the present invention to detect chosen gases. The pyroelectric camera detects the presence of particular gases by measuring the differential absorption or emission in the infrared region. First one filtered image is exposed to the image tube and then the other. This process is repeated at rates rapid enough to convey the gas image as a real-time video picture which can be seen on an ordinary video monitor. If the two filters are properly matched and the background contains no emissivity differences or thermal differences, then nothing is seen. This is because there is no change at all between the two filtered scenes and, thus, no different signal. By knowing which particular wavelengths are characteristic for each gas it is possible to readily design the two filter areas such that one is at a peak absorption wavelength of the gas while the other is at an unaffected wavelength.

Figure 4:
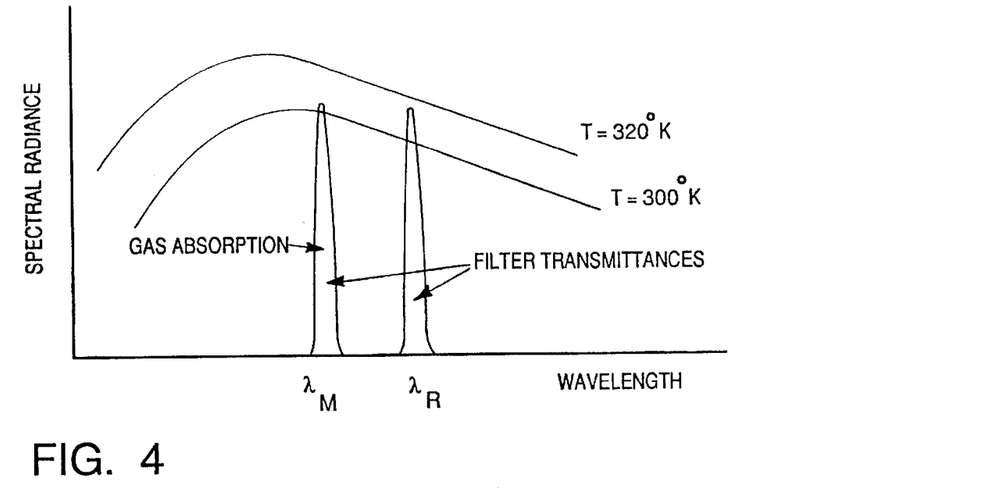
FIG. 4 is a graph showing the Planck radiation function of the chopping filter shown in FIG. 3.

The chopping filter 28 should be made to exacting tolerances both physically and optically. The mechanical balance must be as close to perfect as possible in order to minimize vibration. The optical densities of the filter areas should be set so that the energy balances out when there is no gas present, producing a net output of zero from the detector. This is important because the wavelengths of the two filter areas lie at different points on the black body curve, as shown in FIG. 4, and cannot be equal in energy to each other. The density of one section should be carefully adjusted relative to the other section so that the effect of the black body curve is minimized.

The operation and requirements of the chopping filter 28 can also be described mathematically. The spectral radiance of the scene, which includes both gas at a temperature $T_G$ and a background at a temperature $T_B$ is given by the following equation:

$$N(\lambda, T) = N_G(1 - e^{-\alpha CL}) + N_B e^{-\alpha CL} \quad (1)$$

Where N is the spectral radiance of the scene, G and B refer to the gas and background, respectively, $\alpha$ is the absorption coefficient, C is the gas concentration and L is the gas cloud length. Atmospheric absorption has been ignored in equation (1) above. The first term in equation (1) is spectral radiance of the gas re-emitting the amount absorbed from the background. The second term in equation (1) is the spectral radiance of the background after absorption by the gas.

As discussed above, the filter areas on the chopping filter 28 have their transmissions peaked at a measuring wavelength which is absorbed by the gas and at a reference wavelength which is not absorbed by the gas. Since the infrared camera responds to difference in spectral radiances, the relevant equation is:

$$\Delta N = N_G(\lambda_M) - N_B(\lambda_R) + [N_B(\lambda_M) - N_G(\lambda_R)]e^{-\alpha CL} \quad (2)$$

where $\lambda_M$ is the measuring wavelength and $\lambda_R$ is the reference wavelength for the particular chopping filter.

The contrast is the difference between the target radiance and the background radiance divided by the sum of the radiances. For the chopping filter of the present invention, the contrast R is given by:

$$R = \frac{[N_G(\lambda_M) - N_B(\lambda_M)][1 - e^{-\alpha CL}]}{N_G(\lambda_M)(1 - e^{-\alpha CL}) + N_B(\lambda_M)(1 + e^{-\alpha CL}) - 2N_B(\lambda_R)} \quad (3)$$

When the effective temperature difference between the gas and the background is zero, i.e., when $N_G(\lambda_M) = N_B(\lambda_M)$ and $N_G(\lambda_R) = N_B(\lambda_R)$, then R=0. For high gas concentrations, when $e^{-\alpha CL} = 0$, then the contrast is given by:

$$R = \frac{N_G(\lambda_M) - N_B(\lambda_M)}{N_G(\lambda_M) + N_B(\lambda_M) - 2N_B(\lambda_R)} \quad (4)$$

This contrast is maximized by having $N_B(\lambda_M) = N_B(\lambda_R)$. This effect can be achieved by adjusting the transmission of the filter areas to allow for the difference in the Planck function at the two wavelengths, referring once again to FIG. 4. While this can be achieved precisely only for specific temperatures, the temperature dependence is such that effective equality in radiance can be achieved over a moderate range of temperatures.

The video image processor 18 shown in FIG. 1 is used to enhance the output image of the infrared video camera and to quell the inevitable noise developed in the system. All sensitive detectors and amplifiers, such as the system of the present invention, show significant noise when operated at the high gains needed for such sensitive operation. The goal is to characterize the differences between the signal and the noise and extract the desired signal, particularly when the unwanted noise can exceed the desired signal by magnitudes of 1,000 or more. This extraction process is accomplished by identifying what is consistent about the noise and what is different about the signal. The unique and known qualities of the signal are used as identifiers to sift the noise from the signal. The signal from the infrared video camera, when imaging in the presence of gas, has several such identifiers that may be exploited to remove noise from the camera's output signal. The computerized processing in the image processor makes it possible to produce a crisp, clean image even in very adverse signal-to-noise ratio conditions.

The first identifier used in the present system is the gas cloud's property of constant change or constant movement; its boundaries are constantly in a state of flux. This constant change can be detected by subtracting image frames from each other. When frames are subtracted from each other, nothing that is constant remains; only changes are carried forward. This operation is very useful in image processing because it eliminates any fixed pattern noise or differential signal due to background objects in the picture. Since the objective of the infrared video camera is to image gas clouds only, all background objects are considered to be noise. After this processing step, only gas cloud changes and random noise will remain in the picture. This is a great reduction of information to be processed in further steps.

Another special characteristic of flowing gas is that it has a grouped or "blobby nature", or an appearance, once it is made visible, that can be referred to as "cloud-like". In essence, this means that while the boundaries of the gas cloud are constantly changing, its interior is relatively consistent. Thus, it is continuous in its interior area and may be detected because of that feature. Random noise, on the other hand, has a nature of non-continuous behavior and changes randomly from one moment to the next. Several processing steps take advantage of this cloud-like nature of the gas.

Figure 5:
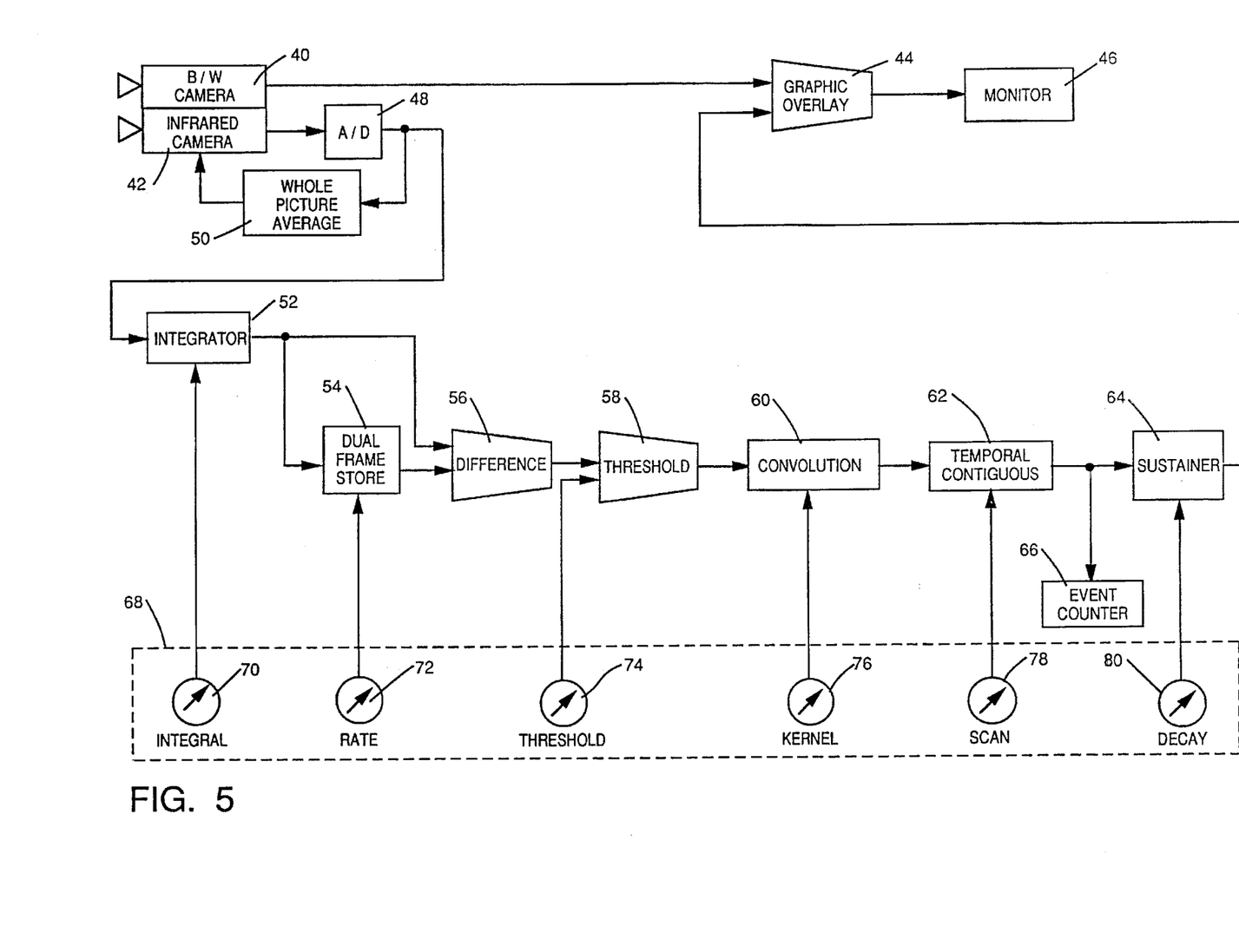
FIG. 5 is a schematic diagram of the preferred image processor used in the present invention.

The preferred image processor used in this system is shown in detail in FIG. 5. As discussed above, a conventional, visual light video camera, such as a black and white video camera 40, is positioned preferably co-located close to or adjacent an infrared video camera 42. Other physical arrangements for the video cameras 40, 42 are possible, such as separating the cameras, or using a shared lens and beamsplitting arrangement with combined cameras, as long as the two video cameras 40 and 42 view substantially the same scene. The output signal developed by the black and white visible light camera 40, representing the visible image of the scene, is supplied directly to a graphic overlay 44 which combines the output signal of the black and white camera 40 with the output signal of the infrared camera 42 after the infrared camera output signal has been subjected to processing as will be discussed hereinafter. The combined output signals from the black and white camera 40 and the infrared camera 42 are then supplied to a color video monitor 46 which provides the desired view of the gas cloud superimposed on the background view observed by the cameras. In a preferred embodiment, the gas cloud will be shown as a red or brightly colored image superimposed upon a black and white background image. This arrangement provides a stark and readily apparent image on the monitor 46 for easily detecting the location, size and movement of the gas cloud.

Since the processor is preferably contained on printed circuit boards which operate in conjunction with a high speed digital computer, the output signal generated by the infrared camera 42 is first digitized through an analog-to-digital converter 48. The output of this converter 48 is a digitized 256×256 pixel array.

A consequence of running a sensitive gas camera at very high gains and comparing subsequent pictures over time is that very minor drifts can cause significant and erroneous results. These drifts are almost impossible to avoid over the temperature ranges and periods of time to which the infrared camera 42 is subjected. To overcome this problem, the present system includes a form of automatic compensation that keeps the camera stabilized over time. As shown in FIG. 5, the output of the analog-to-digital converter 48 is fed back through a whole picture average block 50 to the infrared camera 42. The whole picture average block 50 functions to calculate a whole picture average continuously so that a base line can be measured. The stability of the camera can be maintained in real-time by using the black level control input on the infrared camera 42. Basically, the whole picture average block 50 functions as a way to monitor the overall picture brightness level. It works by summing the amplitude values of all of the pixels in each video field and dividing the sum by the number of fields used to make this sum. The whole picture average block 50 is useful in the present invention in that the presence of gas will modify the sum to a higher or lower value than it was before the introduction of the gas. It is also useful in regulating the long-term drift of the infrared camera 42.

The whole picture average block 50 can be defined as a computerized control of the black level of the infrared camera 42 in a servo loop which regulates the infrared camera 42 closely over time. Any drift in black level is sensed immediately by integration circuitry in the whole picture average block 50 and is corrected by means of a digital-to-analog converter therein which has its output fed back into the black level control circuits of the infrared camera 42. The chief significance of controlling the black level of the infrared camera 42 is the ability to subtract camera frames from a single image taken at an earlier time. This operation permits extreme sensitivity to even the slowest moving of features that are totally lost by subtracting consecutive frames from each other. If the natural drift of the infrared camera 42 were to remain unchecked, significant information regarding a gas cloud might be overlooked since the difference between past images and the present image would always be significant just from the camera drift itself.

The output signal of the analog-to-digital converter 48 is then supplied to an integrator 52 which integrates two or more successive frames together before further processing is carried out. Noise can be significantly diminished without harming the desired signal by integrating the signal over several frame intervals. Since noise is a random event, integration reduces it. The output of the integrator 52 is supplied to a dual frame store 54 which holds a selected, past reference frame to which subsequent input frames are compared.

As discussed above, one basic concept of the present invention is that frame subtraction will give the needed movement data for the gas cloud. As shown in FIG. 5, the output of the integrator 52 is supplied also directly to a difference block 56, and the output of the dual frame store 54 is supplied to the difference block 56. The difference block 56 functions to subtract the currently detected signal, as supplied from the integrator 52, from a stored past reference signal in the dual frame store 54 on a continuous frame-by-frame basis.

The output of the difference block 56 is supplied to a threshold detector 58 which compares the output of the difference block 56 to a preset threshold level. The threshold detector 58 determines what magnitude of difference detection is significant and should be considered as a possible valid gas cloud signal for further processing.

The signal that represents the gas cloud, which the image processor is attempting to isolate, is represented by certain consistencies that noise accompanying the signal does not have. These consistencies exist both spatially and temporally. By constructing a processor tuned to these consistencies, the desired signal can be almost totally isolated from the noise with little loss of signal. In order to take advantage of these consistencies of a gas cloud, the output of the threshold detector 58 is supplied to a convolution block 60 which conducts a spatial filtering process on the signal. The output of the convolution block 60 is then supplied to a temporal contiguous block 62 for temporal processing of the signal.

The spatial filtering process carried out in convolution block 60 is based upon the principle that a gas is usually gathered together into a group or a block, which allows filtering to be accomplished on areas of high spatial concentration. To accomplish this in the present invention, 3×3 pixel areas are swept across all areas of the image in each frame in order to detect grouped areas and certain spatial shapes of groups. There are various methods which could be used for detecting the desired spatial characteristics. One method would be to count the number of activated or fired pixels in this nine pixel area. A high count, such as having five or six of the nine pixels fired, would be indicative of a blob or a gas cloud. In another technique, specific shapes would be sought within the 3×3 pixel area rather than just relying upon the fired pixel count. For example, three pixels in the block representing a vertical column can be sought. This technique allows for a low count with greater sensitivity while being insensitive to noise which is predominantly a horizontal phenomenon in the raster scanning which accompanies the generation of the frames. When noise occurs, it is likely to involve several pixels on a line adjacent to each other because of ringing and other transmission line type effects. This type of noise artifact would never manifest itself in adjacent raster lines because of the long time interval between the lines.

Figure 6A:
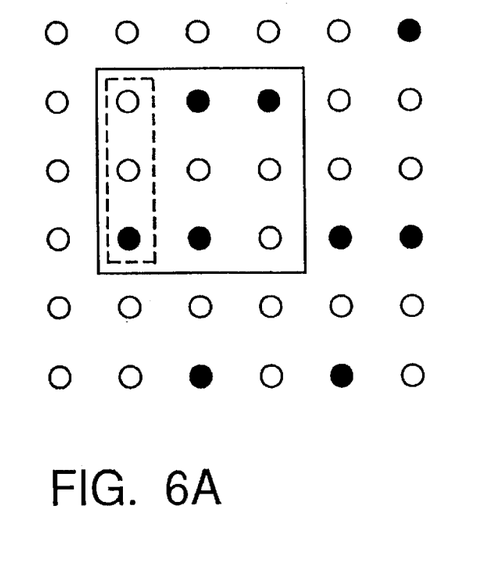
FIG. 6A and FIG. 6B are schematic diagrams showing the signal processing carried out in the convolution block of FIG. 5.
Figure 6B:
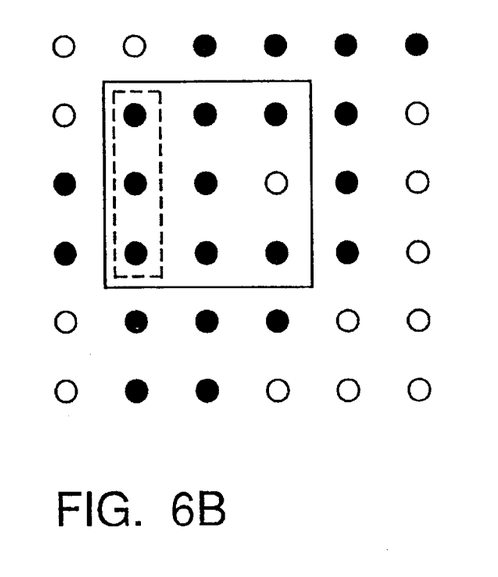

The preferred method for carrying out the spatial filtering in the convolution block 60 is shown in FIGS. 6A and 6B. In FIGS. 6A and 6B, a small open circle represents an unfired pixel in the pixel array, while a solid circle represents an active or fired pixel representing a portion of the image under detection which satisfies the earlier steps of the processor. A solid square has been drawn around a 3×3 array of pixels. For determining whether to fire one of the pixels in this block, such as the pixel in the upper left-hand corner, the convolution block 60 will examine the left-hand-most vertical column, identified by a surrounding dashed rectangle. Under the criteria established in the present invention, a significant or gas related event is considered to have occurred only if the three vertical pixels in the left-hand-most column of the 3×3 pixel array are all active or fired. As shown in FIG. 6A, only one of the pixels within the left-hand-most vertical column is fired. This will result in the upper left-hand-most pixel of the block remaining not fired or activated after the spatial filter processing in the convolution block 60. While this example does look at the upper left-hand-most pixel of the 3×3 array, a determination for firing any of the pixels in this array can be used by the left-hand-most vertical column. It is only important that the same pixel within the 3×3 array be used for all of the subsequent evaluations. In the 3×3 array of pixels shown in FIG. 6A, the left-hand-most column has all three of its pixels active or fired. This would cause the upper left-hand-most pixel of the 3×3 array to be fired.

The temporal processing carried out in the temporal contiguous block 62 is similar to the spatial processing except that it responds to the grouping of pixels over time rather than in space. The underlying theory is that gas cloud related pixels should exist over a sustained period of time if they are true gas signals, and would not if they were created from noise. Processing in the temporal contiguous block 62 fires a particular pixel in a particular frame only if the prior processing steps determined that an event occurred in that pixel for a certain number of previous frames. Only if the event occurred in the desired number of frames would the particular pixel be fired for further processing.

The output from the temporal contiguous block 62 is then supplied to a sustainer 64 which maintains each pixel as fired or active for a particular period of time. It was discovered that a fired signal, once detected, occasionally did not provide a continuous, smooth display. Instead, the display showed a spotty or blotchy output. This visual defect is overcome with the addition of the sustainer 64 which effectively extends the display for several subsequent video frame intervals. This feature is used solely for the improvement of the appearance of the display and does not affect the extraction of the signal which occurred in the earlier processing steps. The output of the temporal contiguous block 62 is also supplied to an event counter 66 which keeps track of the occurrence of "events" or fired pixels which satisfy all of the processing requirements.

The output of the sustainer 64, which is basically the end result of the processing of the output signal from the infrared camera 42, is supplied directly to the graphic overlay 44. As discussed above, the graphic overlay 44 combines the processed output from the infrared camera 42 with the output signal of the black and white camera 40 and supplies this combined signal to the monitor 46.

Each of the integrator 52, dual frame store 54, threshold detector 58, convolution block 60, temporal contiguous block 62 and sustainer 64 have controls associated therewith on a remote or adjacent control panel 68 or the like. An integral control 70 supplies a signal to the integrator 52 which sets the number of frames which will be integrated before further processing takes place. The integral control 70 can be set from one frame up to nine frames or more, although it has been found that fewer number of frames need be integrated for adequate processing. The rate control 72 is used to set how often a reference frame is stored in the dual frame store 54. This rate can be set to as frequently as once per frame, although such a rapid setting will remove the longer term effects of drift and the like. If the rate is set at a slower rate, for updating at longer intervals, the system becomes extremely sensitive because long-term changes are not eliminated and even small amounts of slow building gas become detectable.

Once processing is under way, the operator can adjust the threshold level by a threshold control 74, which can be a potentiometer supplying a signal level to the threshold block 58. The threshold level set by the threshold control 74 reflects the value at which the difference image data becomes recognized as significant and should be set as low as possible without saturating the picture with noise. The pixel amplitude resolution of the system is 256 bits which, when subtracted from similar resolution pixels, yields a difference value. By setting the value of the threshold control 74 to a low number, nearly any difference between corresponding pixels can be detected. Likewise, the integral control 70 can be set during operation to diminish the noise in the image.

A kernel control 76 on the control panel 68 is used to select which of various predetermined spatial filtering processes will be conducted on the signal. Some of the various options were outlined above, with the preferred spatial filtering being the presence of three fired pixels in the left-hand-most vertical column of a 3×3 pixel array. This 3×3 array was selected because it accomplishes good results in detecting gas clouds, but does not require undue computer processing speed and memory. Larger pixel arrays, such as 4×4, 5×5 and the like can be used, and also other patterns and/or combinations of fired pixels can be used. The various selected options would be programmed into the computer and selected by the kernel control 76.

Similarly, the number of frames that are used in the temporal contiguous block 62 to indicate a significant event can be set by the scan control 78. A response can be made to fired pixel sequences as short as one or as long as sixteen or more pixels in a row. A temporal contiguous test carried out over about eight subsequent frames has been found to be satisfactory for detecting gas clouds. Although decisions can be made based upon responses that occur over durations longer than sixteen pixels in a row, this method might be useful only in situations of extreme noise where holes or non-fired pixels might be made in an otherwise valid signal. Finally, a decay control 80 is used to set the duration for the sustainer 64.

Figure 7:
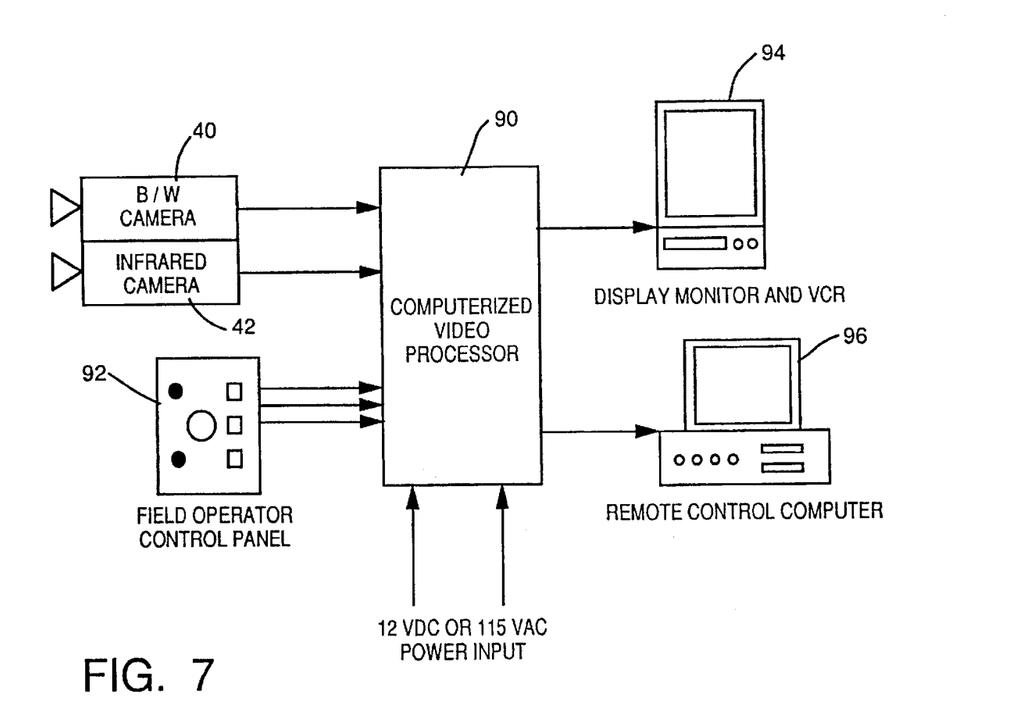
FIG. 7 is a schematic diagram showing a complete gas imaging system in accordance with the present invention.

The present system can be readily incorporated into a complete system as shown in FIG. 7. The video signals developed by the black and white camera 40 and the infrared camera 42 are supplied directly to a computerized video processor 90 as described above in connection with FIG. 5. Appropriate DC or AC power is supplied to the video processor 90. In addition, a field operator control panel 92 can be used to set the adjustable parameters for the video processor 90, as well as supply other data and information thereto. The output signals developed by the computerized video processor 90 can be supplied directly to a display monitor 94 which can also have a video cassette recorder attached thereto or associated therewith for recording the detected signals for further analysis. In addition, the output signals developed by the video processor 90 can be supplied directly to a remote control computer 96 for data storage and later analysis, particularly where unattended monitoring is used. The system can also be designed to include automatic alarms and the like for clearly indicating when certain conditions are detected.

The system discussed above is a passive camera system which is capable of imaging toxic gas or other gas releases in normal working environments. Presently, the system has achieved an imaging capability against temperature differentials of around 5° C. with a sensitivity in the range of fifty ppm-meters. Sensitivity of one ppm-meter has been achieved against heated or cooled background objects.

While the system discussed above is a preferred arrangement for imaging invisible gases, the video image processor discussed can be also used for imaging clouds of visible gas, such as steam, smoke and the like by using a black and white camera in conjunction with the processor without an infrared video camera. In addition, the image processor can be combined with a cooled infrared video camera, which has a fixed filter across its input aperture. All of the advantages of the processing discussed above would be available in that arrangement. Although it is preferred overall to use an uncooled, pyroelectric infrared video camera in this system, with the specially designed chopping filter, the advantages of the processor of this invention would also be obtained by using it with other infrared video cameras. Moreover, the chopping filter can be used with non-pyroelectric infrared cameras, such as photon detector arrays, but the system would need to subtract the signals generated by the different filter areas to develop a difference signal. This difference signal generation or waveband comparison is carried out automatically in pyroelectric infrared video cameras. Furthermore, the present invention contemplates the use of the combined pyroelectric infrared video camera and chopping filter, but with any other video processors.

Having described above the presently preferred embodiments of this invention, it is to be understood that it may be otherwise embodied within the scope of the appended claims.

We claim:

1. Apparatus for generating a visible image of a gas cloud against a background scene, said apparatus comprising:
   a. visible light video camera means for acquiring a visible light video image of a scene;
   b. infrared video camera means for acquiring an infrared video image of substantially the same scene as said visible light video camera means;
   c. chopping filter means associated with said infrared video camera means for alternately presenting band pass filters which pass radiation of two different infrared wavelengths to said infrared video camera means, with a first of said band pass filters passing radiation at a strongly absorbing infrared wavelength for a predetermined gas and with a second of said band pass filters passing infrared radiation at a weakly absorbing infrared wavelength for said predetermined gas;
   d. image processing means responsive to an output from said infrared video camera means for reducing noise inherent therein and enhancing an information signal therein generated by a detected gas cloud, with said image processing means including:
      i. storage means for storing at least one prior output frame of said infrared video camera means;
      ii. comparison means for comparing a current output frame of said infrared video camera means with a prior frame in said storage means and generating a difference signal representing differences between said current frame and said prior frame;
      iii. convolution means responsive to said difference signal from said comparison means for determining, on a pixel by pixel basis for each frame, whether a particular pixel should be further activated based upon a spatial relationship of activated pixels in a surrounding matrix of pixels, including said particular pixel; and
      iv. temporal means responsive to an output generated by said convolution means for activating a pixel only if that pixel is activated in the current frame and was activated in a predetermined number of consecutive prior frames;
   e. overlay means for combining an output from said visible light video camera means with an output from said image processing means and producing a signal representing an image of a gas cloud superimposed upon an image of said background scene; and
   f. display means for displaying the signal generated by said overlay means.

2. The apparatus of claim 1 wherein said infrared video camera means is a pyroelectric infrared video camera.

3. The apparatus of claim 1 wherein said second band pass filter passes infrared radiation at a wavelength close to the wavelength of said first band pass filter.

4. The apparatus of claim 3 wherein said chopping filter is a rotating disc having separate first and second band pass areas therein.

5. The apparatus of claim 4 wherein said chopping filter is a thin, circular wafer of a semiconductor substrate having layers of material deposited thereon to form said first and second band pass filter areas at said strongly and weakly absorbing infrared wavelengths, respectively.

6. The apparatus of claim 5 wherein said band pass filter areas of said chopping filter are formed in the shape of nested, outwardly tapering archimedean spirals separated by about 180°.

7. The apparatus of claim 1 wherein the chopping filter satisfies the equation:

$$N_B(\lambda_M) = N_B(\lambda^R)$$

where, $N_B$ is the spectral radiance of the background scene, $\lambda_M$ is the wavelength characteristic of the first band pass filter and $\lambda_R$ is the wavelength characteristic of the second band pass filter.

8. The apparatus of claim 1 further including a threshold means responsive to the difference signal from said comparison means for supplying to said convolution means only said difference signals which exceed a predetermined threshold level.

9. The apparatus of claim 8 further including an integrator means responsive to the output of said infrared video camera means for integrating at least two frames of said infrared video camera means output before supplying a frame for storage in said storage means and before supplying a current frame to said comparison means.

10. The apparatus of claim 1 further including a sustainer means responsive to an output from said temporal means for maintaining each activated pixel in a frame as activated for a predetermined period of time beyond the duration of said frame.

11. The apparatus of claim 10 further including control means for establishing the rate of frame integration for said integrator means, the rate of storage of frames in said storage means, the threshold level of said threshold means, the spatial filtering method used in said convolution means, the number of consecutive prior frames considered in said temporal means, and the period of time of said sustainer means.

12. The apparatus of claim 1 wherein said convolution means examines a spatial relationship of an n×n array of pixels, where n is an integer greater than 1, including the particular pixel under consideration.

13. The apparatus of claim 1 wherein said convolution means examines a 3×3 array of pixels, including the particular pixel under consideration.

14. The apparatus of claim 13 wherein said particular pixel in a frame is activated only if the three pixels in a left-hand column of said pixel array are each activated.

15. The apparatus of claim 1 further including, in a feedback loop from said infrared video camera means output to said infrared video camera means, a whole picture averager which monitors a baseline brightness level of said infrared video camera means and, in response to any drift in said baseline brightness level, adjusts a black level control in said infrared video camera means to maintain an overall brightness level in said infrared video camera means at a substantially constant level.

16. The apparatus of claim 15 wherein said baseline brightness level is generated by summing the amplitude values of all pixels in one or more frames and dividing the sum by the number of frames utilized.

17. Apparatus for processing a multiple pixel output generated by a video camera to reduce unwanted noise and enhance an underlying information signal contained in said output, said apparatus comprising:
   a. storage means for storing at least one prior output frame of said video camera;
   b. comparison means for comparing a current output frame of said video camera with a prior frame in said storage means and generating a difference signal representing differences between said current frame and said prior frame;
   c. convolution means responsive to said difference signal from said comparison means for determining, on a pixel by pixel basis for each frame, whether a particular pixel should be further activated based upon a spatial relationship of activated pixels in a surrounding matrix of pixels, including said particular pixel; and
   d. temporal means responsive to an output generated by said convolution means for activating a pixel only if that pixel is activated in the current frame and was activated in a predetermined number of consecutive prior frames.

18. The apparatus of claim 17 further including a threshold means responsive to a difference signal from said comparison means for supplying to said convolution means only said difference signals which exceed a predetermined threshold level.

19. The apparatus of claim 18 further including an integrator means responsive to the output of said video camera for integrating at least two frames of said video camera output before supplying a frame for storage in said storage means and before supplying a current frame to said comparison means.

20. The apparatus of claim 17 further including a sustainer means responsive to an output from said temporal means for maintaining each activated pixel in a frame as activated for a predetermined period of time beyond the duration of said frame.

21. The apparatus of claim 20 further including control means for establishing the rate of frame integration for said integrator means, the rate of storage of frames in said storage means, the threshold level of said threshold means, the spatial filtering method used in said convolution means, the number of consecutive prior frames considered in said temporal means, and the period of time of said sustainer means.

22. The apparatus of claim 17 wherein said convolution means examines a spatial relationship of an n ×n array of pixels, where n is an integer greater than 1, including the particular pixel under consideration.

23. The apparatus of claim 17 wherein said convolution means examines a 3×3 array of pixels, including the particular pixel under consideration.

24. The apparatus of claim 23 wherein said particular pixel in a frame is activated only if the three pixels in a left-hand column of said pixel array are each activated.

25. The apparatus of claim 17 further including, in a feedback loop from said video camera output to said video camera, a whole picture averager which monitors a baseline brightness level of said video camera and, in response to any drift in said baseline brightness level, adjusts a black level control in said video camera to maintain an overall brightness level in said video camera at a substantially constant level.

26. The apparatus of claim 25 wherein said baseline brightness level is generated by summing the amplitude values of all pixels in one or more frames and dividing the sum by the number of frames utilized.

27. Apparatus for generating a visible image of a gas cloud comprising:
   a. a video camera; and
   b. image processing means for processing a multiple pixel output generated by said video camera to reduce unwanted noise and enhance an underlying information signal representing said gas cloud, said image processing means including:
      i. storage means for storing at least one prior output frame of said video camera;
      ii. comparison means for comparing a current output frame of said video camera with a prior frame in said storage means and generating a difference signal representing differences between said current frame and said prior frame;
      iii. convolution means responsive to said difference signal from said comparison means for determining, on a pixel by pixel basis for each frame, whether a particular pixel should be further activated based upon a spatial relationship of activated pixels in a surrounding matrix of pixels, including said particular pixel; and
      iv. temporal means responsive to an output generated by said convolution means for activating a pixel only if that pixel is activated in the current frame and was activated in a predetermined number of consecutive prior frames.

28. The apparatus of claim 27 wherein said video camera is an infrared video camera.

29. The apparatus of claim 27 wherein said video camera is a pyroelectric infrared video camera.

30. The apparatus of claim 27 wherein said video camera is a visible light video camera.

31. The apparatus of claim 27 further including a threshold means responsive to a difference signal from said comparison means for supplying to said convolution means only said difference signals which exceed a predetermined threshold level.

32. The apparatus of claim 31 further including an integrator means responsive to the output of said video camera for integrating at least two frames of said video camera output before supplying a frame for storage in said storage means and before supplying a current frame to said comparison means.

33. The apparatus of claim 27 further including a sustainer means responsive to an output from said temporal means for maintaining each activated pixel in a frame as activated for a predetermined period of time beyond the duration of said frame.

34. The apparatus of claim 33 further including control means for establishing the rate of frame integration for said integrator means, the rate of storage of frames in said storage means, the threshold level of said threshold means, the spatial filtering method used in said convolution means, the number of consecutive prior frames considered in said temporal means, and the period of time of said sustainer means.

35. The apparatus of claim 27 wherein said convolution means examines a spatial relationship of an n×n array of pixels, where n is an integer greater than 1, including the particular pixel under consideration.

36. The apparatus of claim 27 wherein said convolution means examines a 3×3 array of pixels, including the particular pixel under consideration.

37. The apparatus of claim 36 wherein said particular pixel in a frame is activated only if the three pixels in a left-hand column of said pixel array are each activated.

38. The apparatus of claim 27 further including, in a feedback loop from said video camera output to said video camera, a whole picture averager which monitors a baseline brightness level of said video camera and, in response to any drift in said baseline brightness level, adjusts a black level control in said video camera to maintain an overall brightness level in said video camera at a substantially constant level.

39. The apparatus of claim 38 wherein said baseline brightness level is generated by summing the amplitude values of all pixels in one or more frames and dividing the sum by the number of frames utilized.

* * * * *

UNITED STATES PATENT AND TRADEMARK OFFICE
CERTIFICATE OF CORRECTION

PATENT NO. : 5,656,813
DATED : August 12, 1997
INVENTOR(S) : Gerald Moore et al.

It is certified that error appears in the above-indentified patent and that said Letters Patent is hereby corrected as shown below:

Claim 7 Column 14 Line 26 $(\lambda^R)$ should read $--(\lambda_R)--$.

Signed and Sealed this

Second Day of December, 1997

Attest:

BRUCE LEHMAN

Attesting Officer

Commissioner of Patents and Trademarks